US00PP13103P2

(12) United States Plant Patent
Olesen et al.

(10) Patent No.: US PP13,103 P2
(45) Date of Patent: Oct. 22, 2002

(54) MINIATURE ROSE PLANT NAMED 'POULBERTY'

(76) Inventors: L. Pernille Olesen, Hillerødvejen 49, DK-3480 Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 23 days.

(21) Appl. No.: 09/655,259

(22) Filed: Sep. 5, 2000

(51) Int. Cl.[7] ..... A01H 5/00
(52) U.S. Cl. ..... Plt./116
(58) Field of Search ..... Plt./116, 118, 119

(56) References Cited

PUBLICATIONS

Community Plant Variety Office, "Certificate on the Grant of Community Plant Variety Rights" Jun. 19, 2000, 6 pages. EU.

UPOV–ROM, 2001/03, Plant Variety Database, GTI Jouve Retrieval Software, 2 citations for 'POULberty'.*

Cooper, "Biotechnology and the Law", (2000, Clark Boardman Callaghan) vol. 2, pp. 8–15 to 8–16.*

Community Plant Variety Office, "Certificate on the Grant of Community Plant Variety Rights" Jun. 19, 2000, 6 pages. EU.

* cited by examiner

*Primary Examiner*—Howard J. Locker

(57) ABSTRACT

A new miniature rose plant which has abundant, flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between an unnamed seedling and 'POULjol'. The two parents were crossed and the resulting seeds were planted in a controlled environment. The new variety is named 'POULberty'.

The new rose may be distinguished from its seed parent, an unnamed seedling, by the following combination of characteristics:

1. The unnamed seedling seed parent is a yellow miniature, where POULberty has yellow blooms with pink intonations.

2. The growth of the unnamed seed parent tends to be upright, where that of POULberty is broad and bushy.

The new variety may be distinguished from its pollen parent, 'POULjol', created by the same inventors, by the following combination of characteristics:

1. The blooms of 'POULjol' are yellow, where those of 'POULberty' are yellow, with pink intonations.

The objective of the hybridization of this rose variety for commercial culture was to create a new and distinct variety with unique qualities, such as:

1. Uniform and abundant flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

The combination of qualities of this variety represents significant improvement over previously available commercial cultivars of this type and distinguishes 'POULberty' from all other varieties of which we are aware. As part of their rose development program, L. Pernille Olesen and Mogens N. Olesen germinated the seeds from the aforementioned hybridization and conducted evaluations on the resulting seedlings in a controlled environment in Fredensborg, Denmark.

'POULberty' was selected by the inventors as a single plant from the progeny of the hybridization inFredensborg, Denmark in May of 1997.

Asexual reproduction of 'POULberty' by cuttings and traditional budding onto *Rosa multiflora* understock was first done by L. Pernille and Mogens N. Olesen in August of 1997, in their nursery in Fredenborg, Denmark. This initial and other subsequent propagations conducted in controlled environments have demonstrated that the characteristics of 'POULberty' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULberty'. Specifically illustrated in SHEET 1:

1. Flowering stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULberty', as observed in its growth in glasshouses in; Half Moon Bay, Calif. Color references are made using The Royal Horticultural Society (London, England) Colour Chart, 1995, except where common terms of color are used.

For a comparison, several physical characteristics of the rose variety 'POULwen' miniature rose variety from the same inventors described and illustrated in U.S. Plant Pat. No. 11,500 are compared to 'POULberty' in Chart 1.

CHART 1

| | 'POULberty' | 'POULwen' |
|---|---|---|
| Bud Color at ¼ Open: | Orange Group 29C. | Blend of Yellow-Orange Group 15C and Orange-Red Group 30B. |
| Upper Surface of Petal, Open Bloom: | Yellow Group 11D, with marginal intonations of Yellow Group 12A–B. | Yellow Group 13C. |
| Petalage: | 30 to 35 petals under normal conditions. | 35–40 petals under normal conditions. |

Parents: Unnamed Seedling×POULjol.

Classification:

*Botanical.*—*Rosa hybrida.*

*Commercial.*—Miniature.

FLOWER AND FLOWER BUD

Blooming habit: Continuous.

Flower bud:

*Size.*—Upon opening, 20 mm–22 mm in length from base of receptacle to end of bud.

*Bud form.*—Long; pointed ovoid.

*Bud color.*—As sepals unfold, Orange Group 29C, Orange Group 29C at ¼ opening.

*Sepals.*—Yellow-Green Group 144A. Moderate to weak foliaceous appendages on three of the five sepals. Surfaces of sepals slightly pubescent. Stipitate glands are present on edges of the sepals.

*Receptacle.*—Surface: Smooth. Shape: Pear-shaped. Size: 5–6 mm (h)×4 mm (w). Color: Yellow-Green Group 144A.

*Peduncle.*—Surface: Some stipitate glands present. Length: 25 mm average length. Color: Yellow-Green Group 144A. Strength: Upright.

*Borne.*—Generally with one bud per flowering stem.

Flower bloom:

*Fragrance.*—Light.

*Duration.*—As a pot plant, flowers last from 4 to 5 days. As a cut flower 3 to 5 days. Petals fall cleanly away from plant.

*Size.*—Medium for use in a 10 cm pot, which is typical in propagation of the cultivar. Average flower diameter is 30 mm when open.

*Form.*—Shape of flower when viewed from the side: Upon opening, upper part: Convex Upon opening, lower part: Flattened convex. Open flower, upper part: Flattened convex. Open flower, lower part: Flattened Convex.

*Petalage.*—Average range: 30 to 35 petals under normal conditions. Petaloids: none.

Color:

*Upon opening, petals.*—Outermost petals: Upper Surface: Orange Group 27C–D. Reverse Side: Orange Group 27D. Innermost petals: Upper Surface: Basal zone is Yellow-Orange Group 18C–D, Marginal zone is Yellow Group 12B. Reverse Side: Orange Group 27B.

*Upon opening, basal petal spots.*—Outermost petals: Outer Side: Green-Yellow Group 1B. Inner Side: Green-Yellow Group 1B. Innermost petals: Outer Side: Green-Yellow Group 1B. Inner Side: Green-Yellow Group 1B.

*After opening, petals.*—Outermost petals: Upper Surface: Yellow Group 11D, with Marginal intonations of Yellow Group 12A–B. Reverse Side: Yellow Group 11D. Innermost petals: Upper Surface: Yellow Group 11D, with Marginal intonations of Yellow Group 12A–B. Reverse Side: Yellow Group 11D.

*After opening, basal petal spots.*—No distinctive coloration at petal base noted.

General tonality: On open flower Yellow-Orange Group 18C–D towards center of bloom; guard petals being Yellow-Orange Group 23D. No change in the general tonality at the end of the $7^{th}$ day. Afterwards, general tonality is Yellow Group 12C–D.

Petals:

*Petal reflex.*—Moderate.

*Petal edge.*—Uniform.

*Shape.*—Round.

*Petaloids.*—None noted.

*Texture.*—Thick.

*Arrangement.*—Imbricated.

Reproductive organs:

*Pollen.*—Not observed.

*Anthers.*—Size: Small. Color: Yellow Group 15C. Abundance: Average.

*Filaments.*—Color: Yellow Group 15C.

*Stigmas.*—Slightly inferior relative to anthers. Color: Greyed-Yellow Group 160D.

*Styles.*—Color: Greyed-Purple Group 185C immediately below stigmas, fading into White Group 155C and then Yellow-Green Group 145D at the base.

PLANT

Plant growth: Vigorous, compact. When grown as a 10 cm pot plant, the average height of the plant itself is 13 to 17 cm and the average width is 20 to 25 cm.

Stems:

*Color.*—Young wood: Yellow-Green Group 144A. Older wood: Yellow-Green Group 144A.

*Prickles.*—Incidence: Moderate. Size: Average length: 4 mm–5 mm. Color: Greyed-Yellow 162D. Shape: Linear.

*Surface.*—Young wood: Smooth. Older wood: Smooth.

Plant foliage: Normal number of leaflets on leaves in middle of the stem: 5 leaflets.

*Leaf size.*—27 mm (l)×15 mm (w).

*Abundance.*—Very abundant.

*Color.*—Upper Leaf Surface: Yellow-Green Group 147A. Lower Leaf Surface: Yellow-Green Group 147B. Juvenile foliage: Green Group 137B.

Plant leaves and leaflets:

*Stipules.*—Size: 7 mm–10 mm. Color: Green Group 137B. Stipitate glands: Sparsely present on outer edge of stipule.

*Petiole.*—Length: 12 mm–16 mm. Color: Yellow-Green Group 144A. Underneath: Yellow-Green Group 144A. Margins: Green Group 137A.

*Rachis.*—Color: Yellow-Green Group 144A Underneath: Yellow-Green Group 144A Margins: Green Group 137A.

*Leaflet.*—Edge: Serrated. Shape: Ovate. Texture: Thin, very slightly glossy.

Disease resistance: Average resistance to mildew, black spot, and Botrytis under normal growing conditions in Half Moon Bay, Calif.

Cold hardiness: 'POULberty' has been found to be resistant to damage from cold, heat and drought damage in USDA Zone 7.

We claim:

1. A new and distinct variety of rose plant of the miniature class, substantially as herein illustrated and described as a distinct and novel rose variety due to its abundant flowers, vigorous and compact growth, year round flowering under glasshouse conditions, suitability for production from softwood cuttings in pots, and durable flowers and foliage which make the variety suitable for distribution in the floral industry.

* * * * *

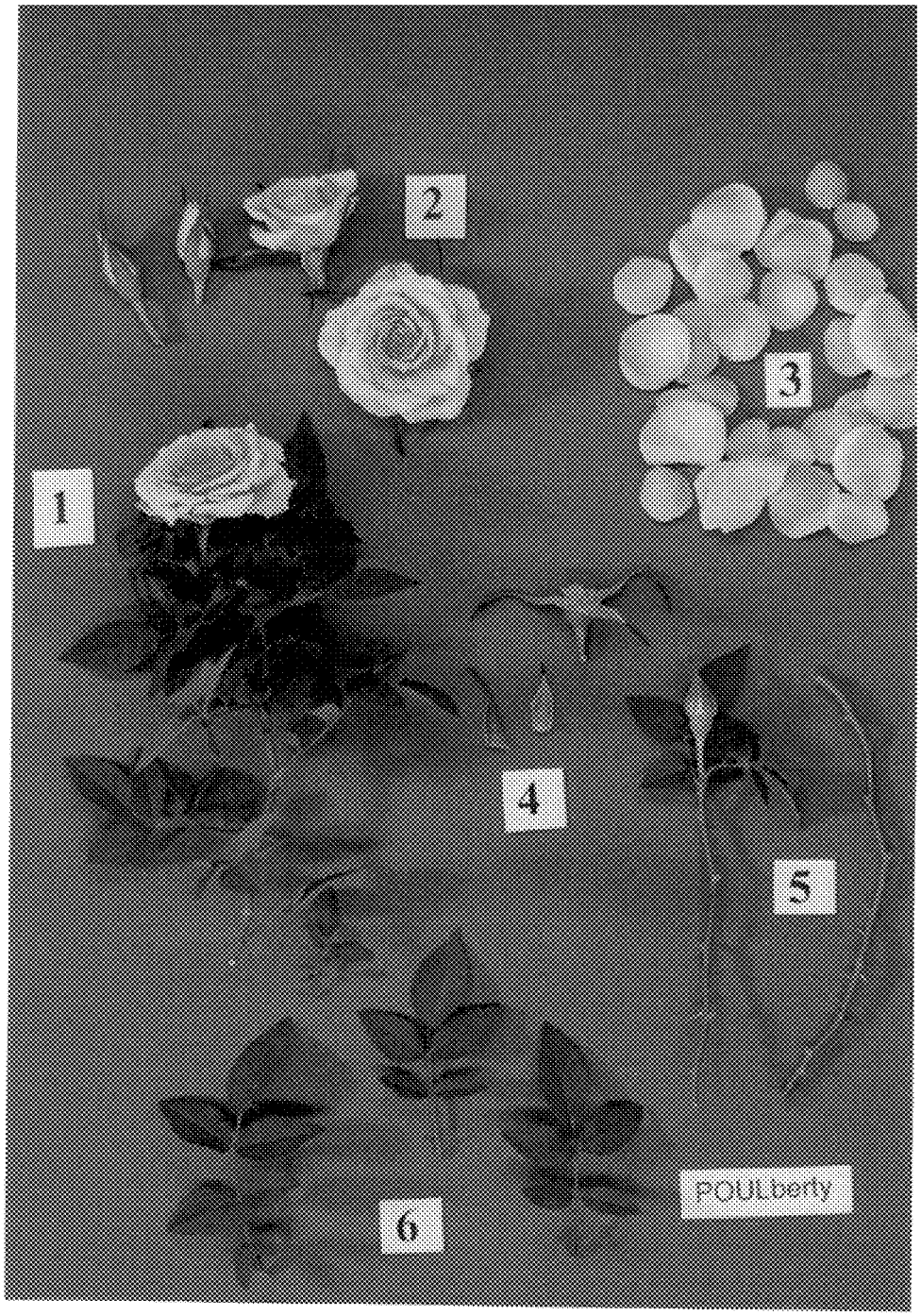
2
3
1
4
5
6
POULberty